Feb. 6, 1973 G. MERRILL Plant Pat. 3,298
PEACH TREE
Filed April 29, 1971
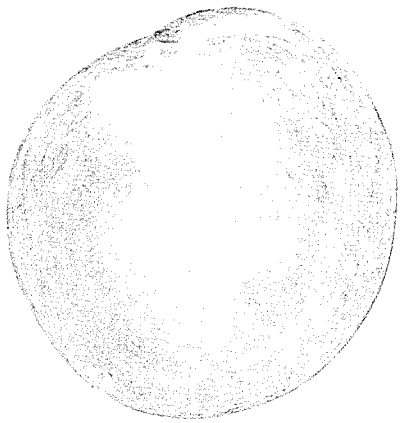
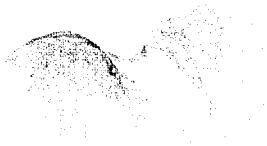
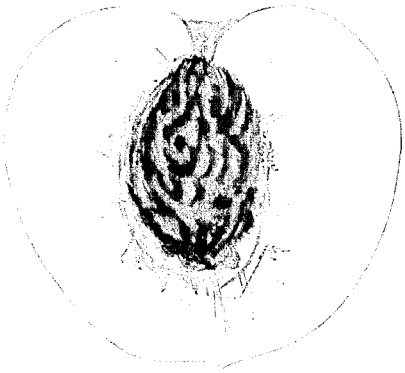
GRANT MERRILL
INVENTOR
Virgil H. Grant
ATTORNEY United States Patent Office Plant Pat. 3,298
Patented Feb. 6, 1973

3,298

PEACH TREE

Grant Merrill, 416 N. Anderson Road,
Exeter, Calif. 93221

Filed Apr. 29, 1971, Ser. No. 138,723
Int. Cl. A01h 5/03
U.S. Cl. Plt.—43 1 Claim The present invention relates to a peach tree and more particularly to a new and distinct variety thereof broadly characterized by a vigorous tree regularly bearing fruit having a brilliant red color over 50 to 75 percent of its skin surface upon an under color of bright yellow when mature, which remains firm and retains its full color on the tree, thus enabling the fruit to be picked in one picking.

The instant variety most nearly resembles its parent plant, Franciscan (U.S. Plant Patent No. 2,239) but is distinguished therefrom by the characteristics of ripening about ten days later and holding its firmness longer than the parent variety and by brighter yellow under color with brighter red blush, and by being completely free from the stone when ripe.

I discovered the present variety of peach (numbered E12–3NW for identification purposes) on the farm owned by me at Exeter, Tulare County, Calif., on Aug. 1, 1967, by growing seeds produced from open pollinated blossoms of a Franciscan peach tree.

The instant variety has been asexually reproduced by grafting test trees in test plots in Tulare and Fresno Counties, Calif. The resulting trees, fruit, leaves and blossoms were exactly the same as the original fruit and tree (E12–3NW) in each case.

The accompanying drawing is an oil painting of a characteristic mature fruit of the subject variety showing the shape and skin color, and by means of a fruit divided on its suture, showing the characteristic flesh color, when fresh, and the shape and color of the stone.

Referring now more specifically to the pomological characteristics of this new and distinct variety of peach tree, the following has been observed under the ecological conditions prevailing in Tulare County, California, and is an outline description thereof. All major color plate identifications are by reference to Maerz and Paul's Dictionary of Color, First Edition.

*Tree*

Size: Large vigorous.
Trunk: Shaggy; color, gray.
Branches: Main branches, shaggy, gray color; younger branches, brown, not shaggy.
Lenticels: Medium in size, numerous.
Twigs: Long with long internodes; green to red-brown in color; smooth.
Productivity: Moderate to heavy bearer, regular producer.

*Leaves*

(Selected from mid-portion of new growth when 18 to 24 inches in length)

Shape: Lanceolate, tip accuminate.
Size: Length 6 to 7 inches for the largest and 2½ to 3½ inches for the smallest, width 1½ to 1¾ inches for the largest to ⅝ to ⅞ inches for the smallest; medium thick.
Color: Dark green on upper surface, lighter green on under surface, veins on under surface very light yellow-green.
Class: Classes 2 and 3. Meader & Blake: Proceedings of the American Society for Horticulture Science, vol. 37, page 203.
Margin: Glandular, crenate.

Petiole: Medium size, generally about ⅜ to ½ inch long.
Character: Deciduous.
Glands: Reniform, on petiole and lower parts of leaf.
Stipules: Present on young leaves, dropping off early.

*Flowers*

Blooms: Large, showy, light pink.
Season: Mid season to late, about with O'Henry (U.S. Plant Patent No. 2,964).
Pollen: Abundant.

*Fruit*

(Described at maturity—1970 growing season)

Season of ripening: About with Improved Pacifica (U.S. Plant Patent No. 2,425); first picking, July 20; last picking, July 30.
Shape: Generally round to slightly heart shaped.
Size: Described when well pruned and thinned: axial diameter 2¾ to 2⅞ inches, transverse in suture plane 2½ to 3 inches, diameter at right angle to suture plane (cheek to cheek) 2½ to 3 inches.
Suture: Shallow to distinct crease; extends from base toward, but discontinues at, apex; slightly deeper at stem end.
Dorsal surface: Rounded, slight depression at pistil point.
Cavity: Medium size, medium abrupt, elongated in suture plane; depth ⅜ to ½ inch, breadth ½ to ¾ inch.
Base: Retuse.
Apex: Mucronate.
Pistil point: Apical, very short to depressed.

*Skin*

Thickness: Medium.
Tenacity: Tenacious to flesh.
Texture: Medium tender.
Flavor: Sweet.
Color: Lighter side; undercolor light yellow 9–L–5 to orange yellow Mikado 9–J–9, with red blush varying from 1–I–11, 1-K-11, and 4–L–6 Red Cross to darker 6–L–6 Chianti; darker side: yellow undercolor 9–L–5 with red blush varying from Aurora 1–G–10 to Afghan Red 5–L–6.
Pubescence: Slight.

*Flesh*

Color: Uniform Apricot yellow 9–K–5 with Cardinal red 5–L–6 near stone.
Juice: Rich.
Texture: Meaty when firm, soft to meaty when soft.
Fibers: Fine, moderate.
Ripens: Evenly.
Flavor: Delicate.
Firmness: Evenly firm throughout, retains firmness on the tree until highly mature.
Aroma: Slight.
Eating quality: Good.

*Stone*

Tenacity: Completely free from flesh when ripe.
Size: Medium; length 1 5/16 to 1½ inches, width ⅞ to 1⅛ inches.
Form: Obovate, tip accuminate, base straight to oblique, hilum oval.
Surface: Irregularly pitted and furrowed throughout with pits round to oval.
Dorsal edge: Narrow; usually one deep groove from base, often discontinuous toward apex.
Ventral edge: Mostly thick with fine furrows, but variable.
Color: When fresh, from Raw Sienna 13–L–10 to dark brown 48–L–1.
Tendency to split: None.

*Use*

Shipping quality: Good, nearby or long distance, general market.

Although the new variety of peach tree possesses the described characteristics under the ecological conditions prevailing in Tulare and Fresno Counties, Calif., having first been discovered near Exeter, Tulare County, it is to be understood that variations of the usual magnitude in characteristics incident to the growing conditions, pruning, thinning, fertilizing and pest control are to be expected.

Having thus described and illustrated my new variety of peach tree, what is claimed is:

1. A new and distinct variety of peach tree substantially as illustrated and described and being characterized by a vigorous tree regularly bearing fruit which when mature remains firm and retains its full color on the tree, thus enabling it to be picked in one picking, having a brilliant red color over 50 to 75 percent of its skin surface upon an under color of bright yellow, and which most nearly resembles its parent plant, Franciscan (U.S. P.P. 2,239), but differs from and is an improvement on that variety by ripening about ten days later and holding its firmness longer, by its brighter yellow skin color and brighter red blush, and by being completely free from the stone when ripe.

No references cited.

ROBERT E. BAGWILL, Primary Examiner